United States Patent

Adel et al.

[11] Patent Number: 6,142,629
[45] Date of Patent: Nov. 7, 2000

[54] SPECTRAL IMAGING USING ILLUMINATION OF PRESELECTED SPECTRAL CONTENT

[75] Inventors: Michael E. Adel, Zichron Yaakov; Dario Cabib; David Wine, both of Timrat, all of Israel

[73] Assignee: Applied Spectral Imaging Ltd., Migdal Haemek, Israel

[21] Appl. No.: 09/143,964

[22] Filed: Aug. 30, 1998

[51] Int. Cl.[7] ........................................ A61B 3/14
[52] U.S. Cl. ............................................. 351/206
[58] Field of Search ..................... 351/200, 205, 351/206, 211, 221; 600/318, 319; 356/400; 250/461.2, 461.1

[56] References Cited

U.S. PATENT DOCUMENTS 5,433,197  7/1995  Stark ........................................ 600/319
5,760,407  6/1998  Margosiak et al. .................. 250/461.2

*Primary Examiner*—George Manuel
*Attorney, Agent, or Firm*—Mark M. Friedman

[57] ABSTRACT

A device and method for spectral imaging of an object. A plurality of sets of narrow-band light sources such as LEDs are provided. Each set emits illumination radiation in a different narrow spectral band. Each set is activated sequentially to illuminate the object. Light reflected from the object or transmitted by the object is focused on a detector array to image the object. Narrower illumination bands are provided by dispersing the emitted light using a dispersive optical element such as a diffraction grating. Alternatively; selected sets or subsets are activated simultaneously with duty cycles that emulate a preselected spectral distribution. For imaging ocular fundus tissue, the illumination light is shaped into an annular beam by an appropriately shaped waveguide.

65 Claims, 12 Drawing Sheets

SPECTRAL IMAGING USING ILLUMINATION OF PRESELECTED SPECTRAL CONTENT

FIELD AND BACKGROUND OF THE INVENTION

The present invention relates to spectral imaging and, more particularly, to a device and method for acquiring a spectral image of an object by illuminating the object successively, in a plurality of narrow spectral bands, by a plurality of narrow-band light sources, and capturing the image in each narrow band using additional optics such as a digital camera.

In spectral imaging, an image of an object to be studied is acquired at a series of discrete wavelengths, or, more generally, in a series of discrete narrow spectral bands. Two methods of accomplishing this are known, both of which illuminate the object with broad-band light. In the first method, narrow-band output is provided by filtering the light reflected or transmitted by the object, or by dispersing the light reflected or transmitted by the object using a dispersive optical element such as a prism or a diffraction grating. Images of the illuminated object are acquired successively in each spectral band that is passed by the successive filters or by the dispersive optical element. In the second method, the object is illuminated directly by a broad-band light source and, prior to imaging, the light from the object is passed through an interferometer which passes a particular linear combination of spectral bands, depending on the optical path differences (OPDs) of the interfering beams inside the interferometer. These OPDs are varied to obtain a complete set of linear combinations. The result is a set of acquired images of the object at the various linear combinations. Images of the object in the individual spectral bands are obtained from the acquired images by appropriate linear transformations. The second method is described, for example, in U.S. Pat. No. 5,539,517 to Cabib et al., which is incorporated by reference for all purposes as if fully set forth herein.

The relative efficiencies of these two methods have been compared by Felgett, in the context of (non-imaging) spectroscopy. See, for example, R. J. Bell, *Introductory Fourier Transform Spectroscopy*, Academic Press 1972, pp. 23–25 and J. Chamberlain, *The Principles of Interferometric Spectroscopy*, John Wiley & Sons 1979, pp. 305–306, which are incorporated by reference for all purposes as if fully set forth herein. The second method is the more efficient, because under the first method, most of the photons reflected or transmitted by the object are rejected, because of the narrow-band filtering, whereas under the second method, most or all of the photons reflected or transmitted by the object and passed by the interferometer and the imaging optics are collected.

Quantitatively, in the case of noise, such as random noise, that is independent of the signal level, the ratio of the signal-to-noise ratios of the two methods is proportional to the square root of the number of spectral bands:

$$R_2/R_1 \sim M^{1/2} \quad (1)$$

where $R_1$ is the signal-to-noise ratio of the first method, $R_2$ is the signal-to-noise ratio of the second method, and M is the number of spectral bands. In the case of noise proportional to the square root of the light source intensity (photon noise), both $R_1$ and $R_2$ obey $$R_j \sim [(T/M) I \delta\sigma]^{1/2} \quad (2)$$

(j=1 or 2)
where T is the duration of the measurement and $I\delta\sigma$ is the source intensity in a spectral band of width $\delta\sigma$. As a result, $$R_2/R_1 \sim 1 \quad (3)$$

In short, the second method is superior to the first method with respect to noise that is independent of signal level but not with respect to photon noise.

Nevertheless, the second method has certain disadvantages relative to the first method. First, the linear transformations needed to obtain narrow-band images are computationally intensive. A full set of narrow-band images must always be obtained, even if only certain bands are of interest. Second, the objects of interest include portions of live organs, such as the retina or fundus of the eye, which move during the course of the measurement, as the OPDs within the interferometer are varied. This makes it necessary to perform extensive processing of the acquired images before transforming them to narrow-band images, as described in co-pending U.S. patent application Ser. No. 08/942,122. Specifically, the images must be registered spatially, to compensate for the fact that the same pixel in different images does not generally correspond to the same part of a moving object. Furthermore, special Fourier Transform algorithms must be used that account for the fact that, after registration, the OPDs that define the interferograms are not uniformly spaced.

There is thus a widely recognized need for, and it would be highly advantageous to have, a spectral imaging method that would combine the advantages of presently known methods.

SUMMARY OF THE INVENTION

The present invention is similar to the monochromatic prior art method of spectral imaging, but with efficient power utilization. Instead of illuminating the object with broad-band illumination, and discarding most of the reflected or transmitted light, the object is illuminated, for each acquired spectral image, with light having an arbitrary, preselected spectral distribution. In the simplest embodiment of the method of the present invention, this spectral distributions are narrow-band, as in the monochromatic prior art method; but in the most general case, the spectral distributions are matched to the object being imaged.

The following calculations show that a spectral imaging device based on narrow-band light sources has approximately the same performance as a spectral imaging device of the second prior art method with respect to noise that is independent of signal level, and has superior performance with respect to photon noise. These calculations follow the concepts of the above citations from Bell and from Chamberlain.

In the second prior art method, the observation time per narrow spectral band is T/M. If each narrow-band light source of the present invention has the same total illumination flux as the wide-band light sources of the prior art methods, then the integrated signal received in a narrow band $\delta\sigma$ is proportional to T, rather than to T/M. As a result, the signal-to-noise ratio R of the present invention obeys, in the case of noise that is independent of signal level:

$$R \sim T^{1/2} \quad (4)$$

According to Equation (2–18) of Bell, $$R_2 \sim T^{1/2} \quad (5)$$

so that $$R/R_2 \sim 1 \quad (6)$$

With regard to photon noise, the present invention obeys Equation (2) with the source intensity in spectral band $\delta\sigma$ now $MI\delta\sigma$ instead of $\delta\sigma$. Therefore $$R \sim (TI\delta\sigma)^{1/2} \quad (7)$$

so that $$R/R_2 \sim M^{1/2} \quad (8)$$

Consequently, the present invention is expected to have the same performance, with respect to noise that is independent of signal level, as the interferometric prior art method, and has superior performance with respect to photon noise.

From Equations (1) and (6) it follows that, with regard to noise that is independent of signal level, $$R/R_1 \sim M^{1/2} \quad (9)$$

From Equations (3) and (8) it follows that, with regard to photon noise, $$R/R_1 \sim M^{1/2} \quad (10)$$

Therefore, the present invention is expected to be superior to the monochromatic prior art method, both with respect to noise that is independent of signal level, and with respect to photon noise.

Therefore, according to the present invention there is provided a device for spectral imaging of an object, including: (a) a plurality of sets of light sources for producing light in a like plurality of separate spectral bands, each of the sets including at least one of the light sources for emitting light in the spectral band of the each set; (b) an illumination mechanism for directing at least a portion of the emitted light at the object, thereby illuminating the object, the object producing radiated light in response to the illumination; and (c) an imaging mechanism for detecting the radiated light and transforming the radiated light into at least one image of the object.

Furthermore, according to the present invention there is provided a method of imaging an object, including the steps of: (a) producing illumination light in a plurality of spectral bands, using, for each of the spectral bands, at least one light source specific to the each spectral band; (b) illuminating the object with at least a portion of the illumination light, the object producing radiated light in response to the illumination light; and (c) detecting the radiated light so as to produce at least one image of the object.

Furthermore, according to the present invention there is provided a method of imaging eye tissue of an eye including a pupil, including the steps of: (a) producing illumination light in a plurality of spectral bands, using, for each of the spectral bands, at least one light source specific to the each spectral band; (b) forming an annular beam of the illumination light; (c) directing the annular beam at the eye tissue via the pupil to illuminate the eye tissue; (d) collecting light reflected from the eye tissue via the pupil; and (e) detecting the reflected light so as to produce at least one image of the eye tissue.

Furthermore, according to the present invention there is provided a method of imaging an object having at least one of a plurality of features, each of the features having a certain reflectivity spectrum, including the steps of: (a) producing illumination light having a spectral distribution in accordance with at least one of the reflectivity spectra; (b) illuminating the object with the illumination light, the object producing radiated light in response to the illumination; and (c) detecting the radiated light so as to produce at least one image of the object.

Furthermore, according to the present invention there is provided an improved fundus camera of the type in which an annular beam of light is directed at eye tissue and light reflected from the eye tissue travels axially through the annular beam, the improvement including a waveguide having an annular output end wherefrom the annular beam of light emerges.

Furthermore, according to the present invention there is provided a method of imaging an object having a plurality of features, each feature having a reflectivity spectrum from among a larger plurality of reflectivity spectra, including the steps of: (a) producing illumination light at each of a plurality of spectral distributions, each of the spectral distributions being in accordance with at least one of the larger plurality of reflectivity spectra; (b) successively illuminating the object with the illumination light at each of the plurality of spectral distributions, the object producing radiated light in response to the illumination; and (c) detecting the radiated light so as to produce at least one image of the object.

Narrow-band light sources, specifically, light emitting diodes (LEDs), have been used heretofore as light sources for spectroscopy, but not as light sources for spectral imaging. Representative patents in the field include U.S. Pat. No. 3,910,701 to Henderson et al., U.S. Pat. No. 4,566,797 to Kaffka et al., U.S. Pat. No. 5,029,245 to Keränen et al., U.S. Pat. No. 5,257,086 to Fataley et al., U.S. Pat. No. 5,475,221 to Wang et al. and U.S. Pat. No. 5,477,322 to Webster et al. The basic innovation of the present invention is the use of narrow-band light sources for spectral imaging. In the simplest embodiment of the method of the present invention, sets of sources of different narrow-band spectral outputs are used sequentially, to produce narrow-band images. More generally, selected sets of sources are used simultaneously to illuminate the object under study with light of any desired spectral distribution.

The preferred narrow-band light sources of the present invention are LEDs. Typically, the spectral output of an LED is distributed with a particular spectral shape, for example a Gaussian, around a central wavelength. To achieve a narrower spectral width, for example 12.5 nm, the light from the LEDs is dispersed using a dispersive optical element such as a diffraction grating. The relative geometries of the LEDs and the dispersive optical element are such that all the emissions in the desired subsets of the LEDs' bands are directed towards the same common line.

To obtain sufficient illumination intensity, many LEDs with the same spectral output are used together. Sets of LEDs, each set emitting in a different spectral band, are activated successively to provide narrow-band illumination of the object in all desired spectral bands.

Alternatively, selected sets of LEDs are activated simultaneously to illuminate the object with light of a particular spectral distribution. Experience with a particular class of objects may indicate a utility to illuminating the object with light of a particular spectral distribution. For example, the object may belong to a desired class of objects characterized by a feature, with a particular reflectivity spectrum, that distinguishes that class of objects from other classes. An object of unknown classification is illuminated with light whose spectral power distribution is designed in accordance with the reflectivity spectrum of the characteristic feature of the desired class. For example, the spectral power distribution may be the inverse of the reflectivity spectrum of the characteristic feature of the desired class. Objects that belong to the desired class then have spectral images of uniform intensity, as a function of wavelength, in the portions of the images that correspond to the characteristic feature. Objects that belong to other classes have spectral images of nonuniform intensity as a function of wavelength. This has the following three benefits:

1. The dynamic range of the detector is used more efficiently with respect to imaging objects of the desired class. For example, if the spectral power distribution is the inverse of the expected reflectivity spectrum of the characteristic feature, then the reduced variation in reflected intensity with wavelength makes it less likely that the detector is saturated at some wavelengths despite a low signal level at other wavelengths.

2. Measurement time is shortened because the object is illuminated only with the wavelengths of interest, and only in the spectral distributions of interest.

3. It is easier to distinguish features whose reflectivity spectra are used to design the spectral distributions from other features in the same object. Consequently, it is easier to distinguish objects of the desired class from objects that belong to other classes. For example, if the spectral power distribution is the inverse of the expected reflectivity spectrum of the characteristic feature, then the characteristic feature looks spatially and spectrally uniform relative to the rest of the image. In general, the illumination of the object with light of a preselected spectral distribution enables the enhancing of contrast between different features of the object at selected wavelengths.

An important special case of this alternative is applicable to imaging an object having features that may belong to one of a very large number of classes of features with related reflectivity spectra. A mathematical technique called "decorrelation" is used to determine a reduced set of reflectivity spectra that includes, for all practical purposes, all the information inherent in the original set of reflectivity spectra. The object is illuminated successively with spectral distributions that correspond to each of the reflectivity spectra of the reduced set.

Another example of the utility of light of a desired spectral distribution is the case of objects for which the relevant information for object classification exists only in certain spectral bands. For efficient spectral imaging, the irrelevant bands are excluded from the illumination light.

The present invention is particularly suited for the purpose of illuminating an object with light of a desired spectral distribution. The LEDs of spectral bands included in the desired spectral distribution are operated simultaneously, and are turned on and off according to wavelength-dependent duty cycles that result in the object being illuminated with light having the desired effective spectral distribution. As long as each on-off cycle is significantly shorter than the response time of the imaging mechanism, the imaging mechanism integrates over the on and off periods, so that the resulting image is the same as the image that would be obtained if the illumination had the desired spectral distribution at each instant in time. In principle, the same effect can be obtained, using LED sources, by appropriate regulation of the level of electrical current supplied to each LED, and this technique is in fact within the scope of the present invention; but because the output power of an LED is a highly nonlinear function of the input current, it is easier to obtain a desired spectral distribution using a duty-cycle-based output control system than using a current-based output control system.

One important application of the present invention is the spectral imaging of eye tissue in general and the ocular fundus in particular. The prior art device for acquiring monochromatic and wide-band (color) images of the ocular fundus is the fundus camera. In a fundus camera, an annular beam of light is directed into the dilated pupil of the eye. Light reflected from the ocular fundus passes through the pupil and axially through the center of the annulus to imaging optics. According to the present invention, an optical waveguide is configured with a linear input end and an annular output end. The input end of the waveguide is positioned at the common line towards which the narrow-band emissions are directed by the dispersive optical element. The output end is positioned to direct an annular beam towards the eye. Preferably, the optical waveguide is configured as an appropriately shaped bundle of optical fibers.

Conventional fundus cameras use a masked lens and an annular mirror to create the annular beam of light. The scope of the present invention includes a fundus camera that uses an optical waveguide with an annular output end to create the annular beam of light.

Just as the device of the present invention can be incorporated in a fundus camera, to provide light of any desired spectral distribution for spectral imaging of the ocular fundus, so the device of the present invention can be incorporated in any other optical medical imaging apparatus, for example an endoscope. It will be apparent to those skilled in the art how to use the principles of the present invention in endoscopy, for spectral imaging of internal organs.

In addition to the advantages described above with respect to efficient power utilization and with respect to signal-to-noise ratio, the present invention has the following advantages over the monochromatic prior art devices:

1. The monochromatic prior art devices scan wavelength by rotating a filter wheel or by moving a dispersive optical element. The device of the present invention has no moving parts, and therefore is more reliable and easier to maintain than the prior art devices.

2. The monochromatic prior art devices allow the acquisition and/or display of only one monochromatic image at a time. A composite image corresponding to illumination with light of an arbitrary spectral distribution can be synthesized from these images, but not acquired or viewed directly. The present invention is capable of illuminating an object of interest directly with light of a preselected spectral distribution, as described above.

The present invention has the following advantages over the interferometric prior art device of U.S. Pat. No. 5,539, 517;

1. The prior art device scans OPDs by translating or rotating the interferometer or an element thereof. The device of the present invention has no moving parts and therefore is more reliable and easier to maintain than the prior art device.

2. The prior art device requires relatively large computational resources, because a Fourier transform must be performed for every pixel, and because the interferograms that are reduced to spectra contain more data points than the final spectra. The present invention is computationally more efficient than the prior art interferometric method, both in terms of resources and in terms of computational time. Consequently, the present invention is more suited than the prior art method to a clinical setting, in which speed of measurement is advantageous.

3. The OPD of the interferometer of the prior art device varies across the image. In spectral imaging of the ocular fundus, because of eye movements during the measurement, a complex image registration algorithm is needed to compensate for OPD variations, as described in PCT Publication No. WO 98/19293. The device of the present invention acquires the spectrally illuminated images directly, thereby simplifying data presentation.

4. The present invention has the advantage described above, over the prior art device, with respect to the signal-to-photon-noise ratio.

5. The prior art device always measures a complete spectrum. The present invention is capable of measuring only as much of a complete spectrum as is actually needed. In particular, the present invention is capable of illuminating an object of interest with light of a particular preselected spectral distribution, as described above. In the case of sensitive object such as eye tissue, this limits the exposure of the object to potentially damaging illumination.

6. The prior art device is constrained to the relative intensities of the various wavelengths of the measured spectra. It has no mechanism for boosting the signal in dark wavelengths to utilize more efficiently the dynamic range of the detector. In the present invention, this can be accomplished by illuminating the object for a longer period of time at the dark wavelengths than at the bright wavelengths.

7. The LED light sources of the preferred embodiment of the device of the present invention have a mean time between failure that is at least an order of magnitude greater than the preferred quartz-halogen lamp source of the prior art device.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a spectral imaging device and method based on narrow-band light sources. Specifically, the present invention can be used for spectral imaging of a live object such as an ocular fundus.

The principles and operation of spectral imaging according to the present invention may be better understood with reference to the drawings and the accompanying description.

Figure 1:
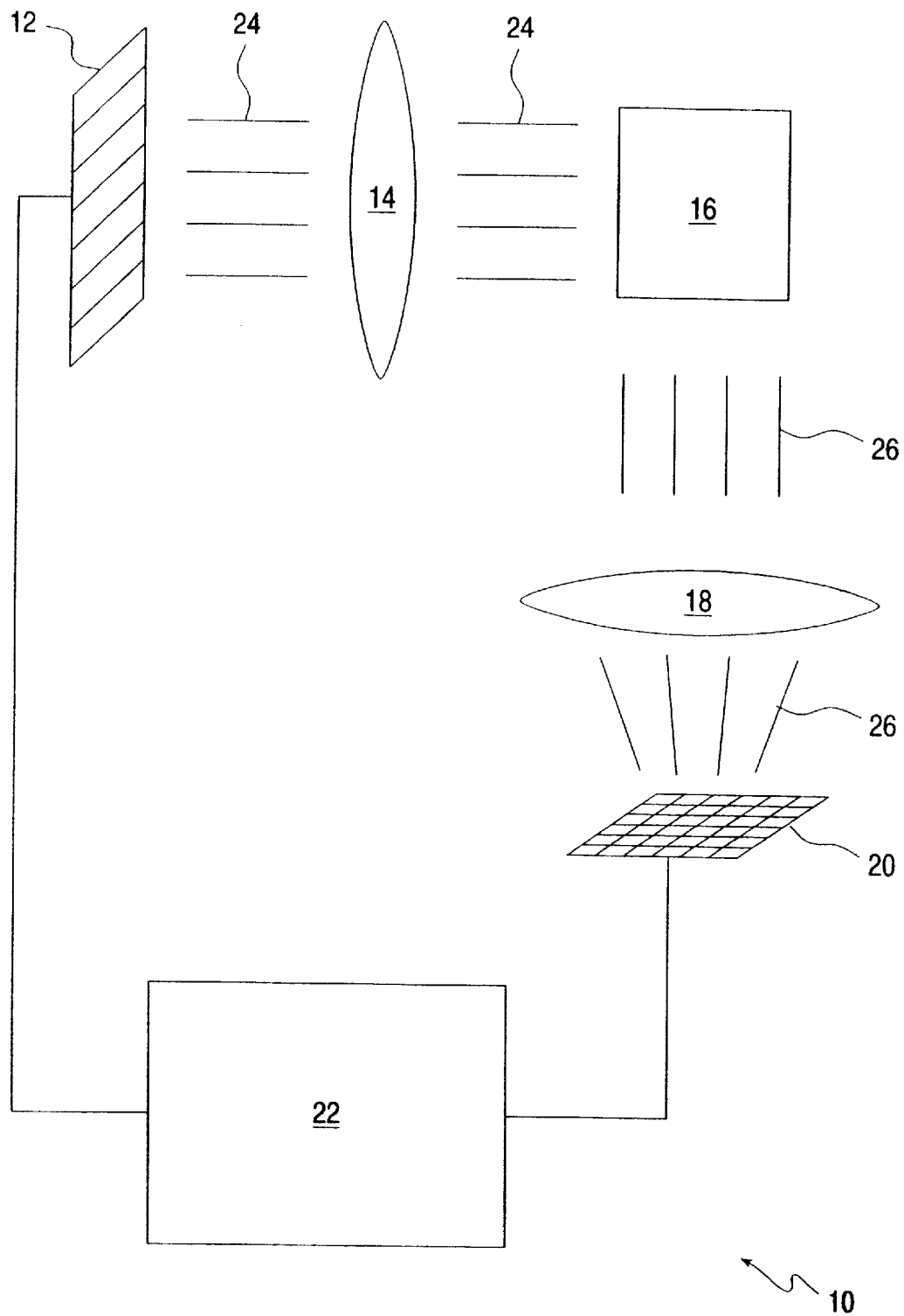
FIG. 1 is a schematic diagram of a spectral imaging device of the present invention.

Referring now to the drawings, FIG. 1 is a schematic diagram of a spectral imaging device 10 of the present invention. A source array 12 of narrow-band light sources emits light 24 which is directed by illumination optics 14 to illuminate an object 16. The interaction of emitted light 24 with object 16 causes object 16 to radiate radiated light 26. Radiated light 26 may be reflected light, transmitted light or scattered light. Radiated light 26 is focused by collection optics 18 onto a detector array 20, which typically is a two-dimensional array of charge-coupled devices. A control system 22 activates the light sources of source array 12 successively to produce emitted light 24 in successive narrow spectral bands. As object 16 is illuminated with emitted light 24 of each spectral band, control system 22 receives the corresponding two-dimensional image of object 16 from detector array 20.

In an alternative embodiment of device 10, detector array 20 is not used, and collection optics 18 are such that an operator can view the two-dimensional images directly. The operator selects the desired spectral bands using control system 22. In an alternative mode of operation of device 10, described in more detail below, selected light sources of source array 12 are activated simultaneously to produce emitted light 24 of a desired spectral distribution.

Figure 2:
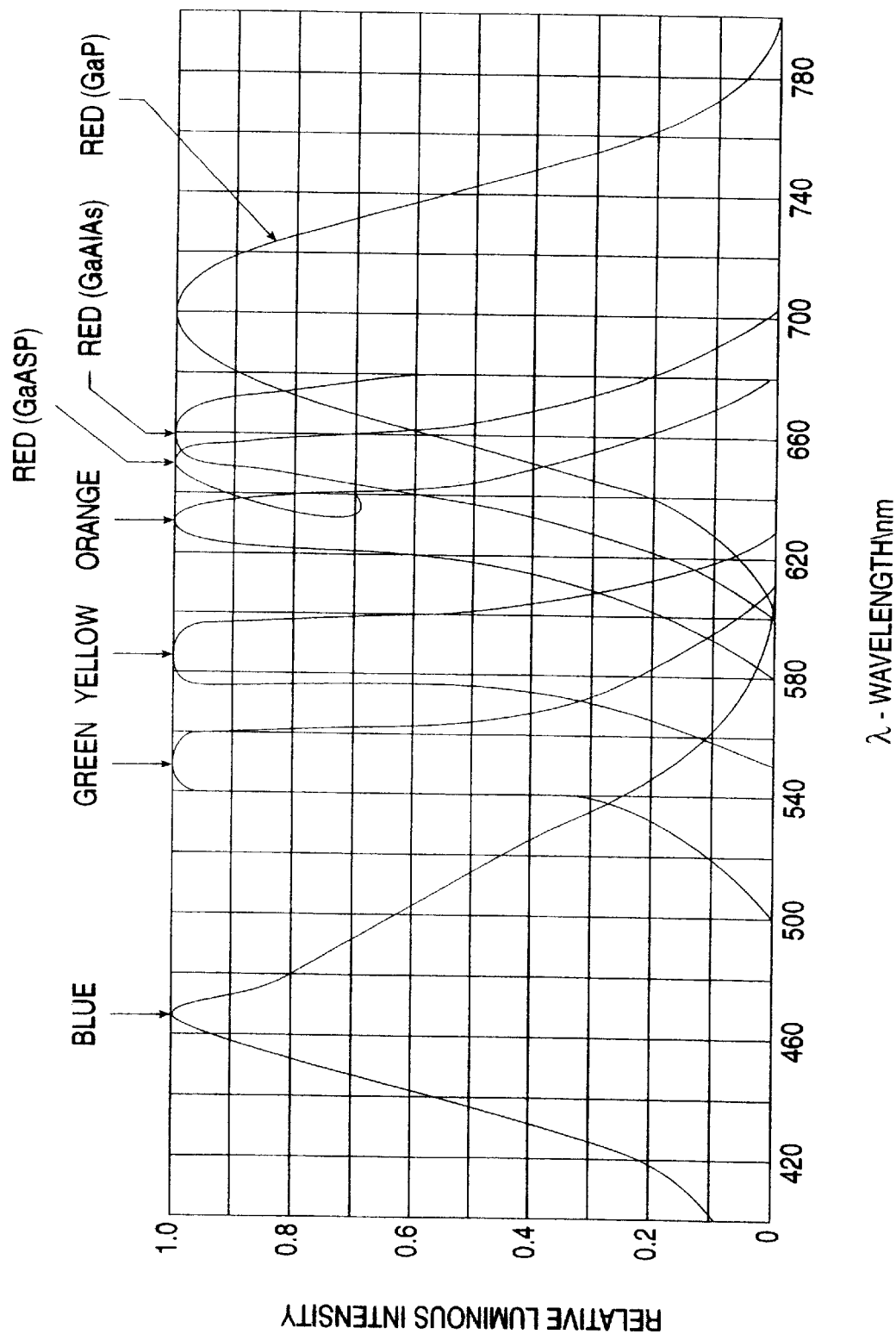
FIG. 2 shows the output spectra of representative LEDs.
Figure 3:
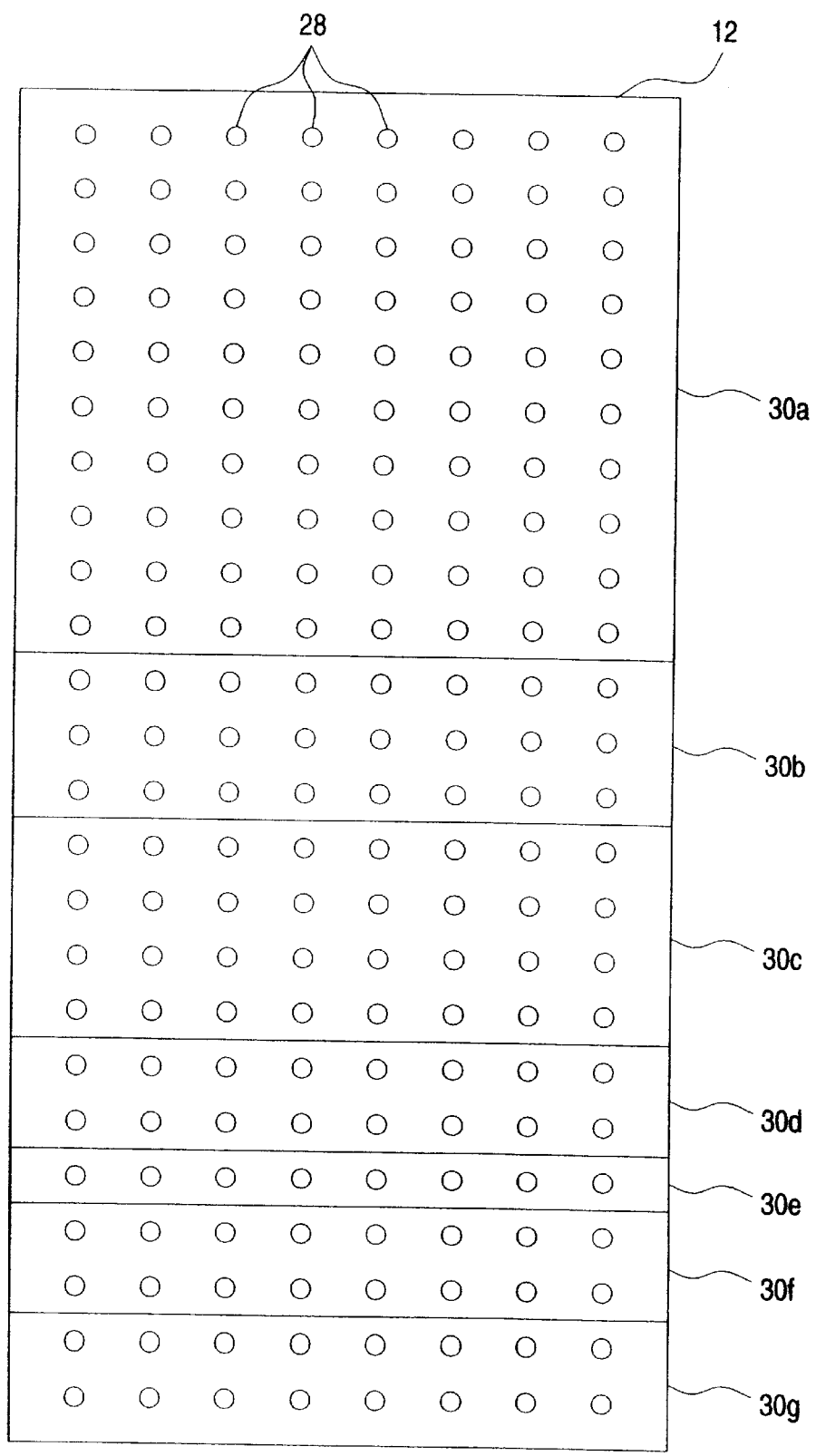
FIG. 3 shows a source array of LEDs.

FIG. 2 shows the spectra of a series of LEDs available from Ledtronics, Inc. of Torrance CF. FIG. 3 shows a preferred source array 12 that uses 192 of these LEDs 28 as narrow-band light sources. LEDs 28 are grouped into 7 sets 30 as follows:

Set 30a (blue LEDs): ten rows, 8 LEDs per row.

Set 30b (green LEDs): three rows, 8 LEDs per row.

Set 30c (yellow LEDs): four rows, 8 LEDs per row.

Set 30d (orange LEDs): two rows, 8 LEDs per row.

Set 30e (GaAsP LEDs): one row of 8 LEDs

Set 30f (GaAlAs LEDs): two rows, 8 LEDs per row.

Set 30g (GaP LEDs): two rows, 8 LEDs per row.

Set 30a covers the spectral range 400 nm to 537.5 nm. Set 30b covers the spectral range 537.5 nm to 562.5 nm. Set 30c covers the spectral range 562.5 nm to 612.5 nm. Set 30d covers the spectral range 612.5 nm to 637.5 nm. Set 30e covers the spectral range 637.5 nm to 650 nm. Set 30f covers the spectral range 650 nm to 675 nm. Set 30g covers the spectral range 675 nm to 700 nm.

Figure 4A:
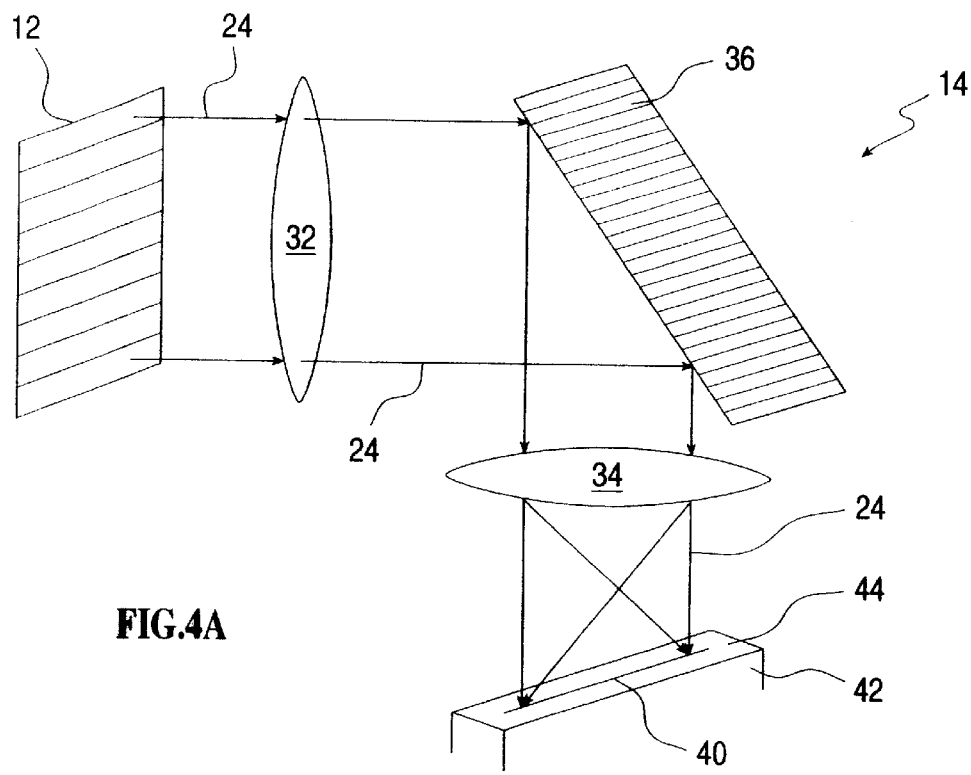
FIGS. 4A and 4B are partial schematic depictions of preferred configurations of the source array and the illumination optics.
Figure 4B:
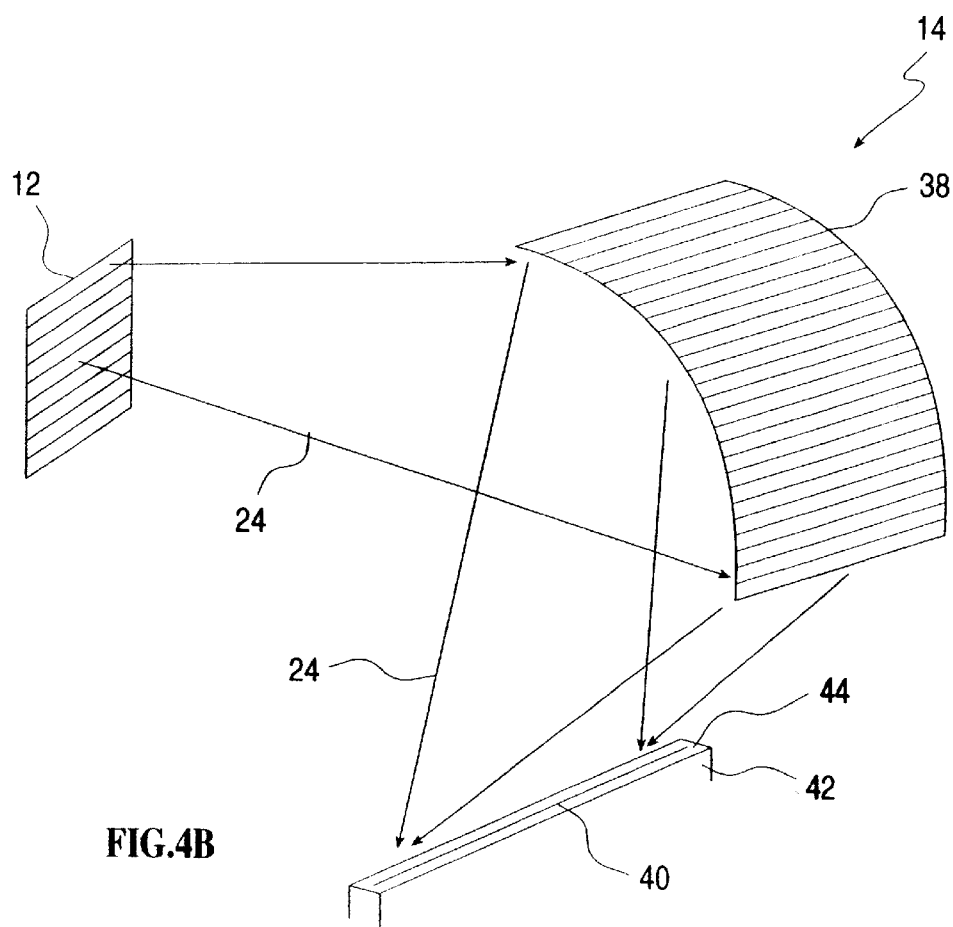

FIGS. 4A and 4B are partial schematic depictions, partly in perspective, of two preferred configurations of source array 12 and illumination optics 14. In the configuration of FIG. 4A, source array 12 is positioned in the focal plane of collimating optics 32. Collimated emitted light 24 is directed towards a planar diffraction grating 36. Diffraction grating 36 is drawn in FIG. 4A as a reflection grating. Alternatively, diffraction grating 36 is a transmission grating. Emitted light 24 dispersed by diffraction grating 36 is imaged by collimating optics 34 onto a line 40. In the configuration of FIG. 4B, a concave diffraction grating 38 disperses emitted light 24 from source array 12 to fall on a line 40. No collimating optics is needed. These configurations are inverses of the usual configuration in spectroscopy, in which white light from a slit is dispersed in a fan by a diffraction grating.

The rows of LEDs 28 and the lines of diffraction grating 36 or 38 all are parallel to line 40. The relative positions of source array 12 and diffraction grating 36 or 38 are chosen so that the desired emitted light from each row of LEDs 28 is directed towards line 40. In fact, only a 12.5 nm wide portion of the spectral band of each row of LEDs 28 is directed towards line 40, thereby providing even narrower spectral bands than are intrinsic to LEDs 28. For example, only light at wavelengths between 400 nm and 412.5 nm from the first row of LED set 30a is directed towards line 40 and only light at wavelengths between 412.5 nm and 425 nm from the second row of LED set 30a is directed towards line 40.

An important advantage of the configurations illustrated in FIGS. 4A and 4B is relative immunity to mechanical and thermal instabilities. The immunity to mechanical instabilities is conferred by the absence of moving parts. The fact that the spectral shape of the output of LEDs 28 is temperature-dependent is rendered largely irrelevant by the fact that the wavelength selected by grating 36 or 38 from each row of LEDs 28 depends only on the geometry of the configuration and not on temperature; all that changes with temperature is the intensity of the light incident on line 40. This variation of intensity with temperature is compensated by a simple precalibration. The rows of LEDs 28 are activated sequentially. An optical fiber is used to conduct light from line 40 to a suitable detector, so that the intensity of light from each row of LEDs 28 can be measured and compared to a reference value. The duty cycle of the LEDs of that row is adjusted accordingly. Alternatively, the temperatures of LEDs 28 are measured directly and compared to calibration curves of intensity vs. temperature, and the duty cycles of LEDs 28 are adjusted accordingly.

Figure 11:
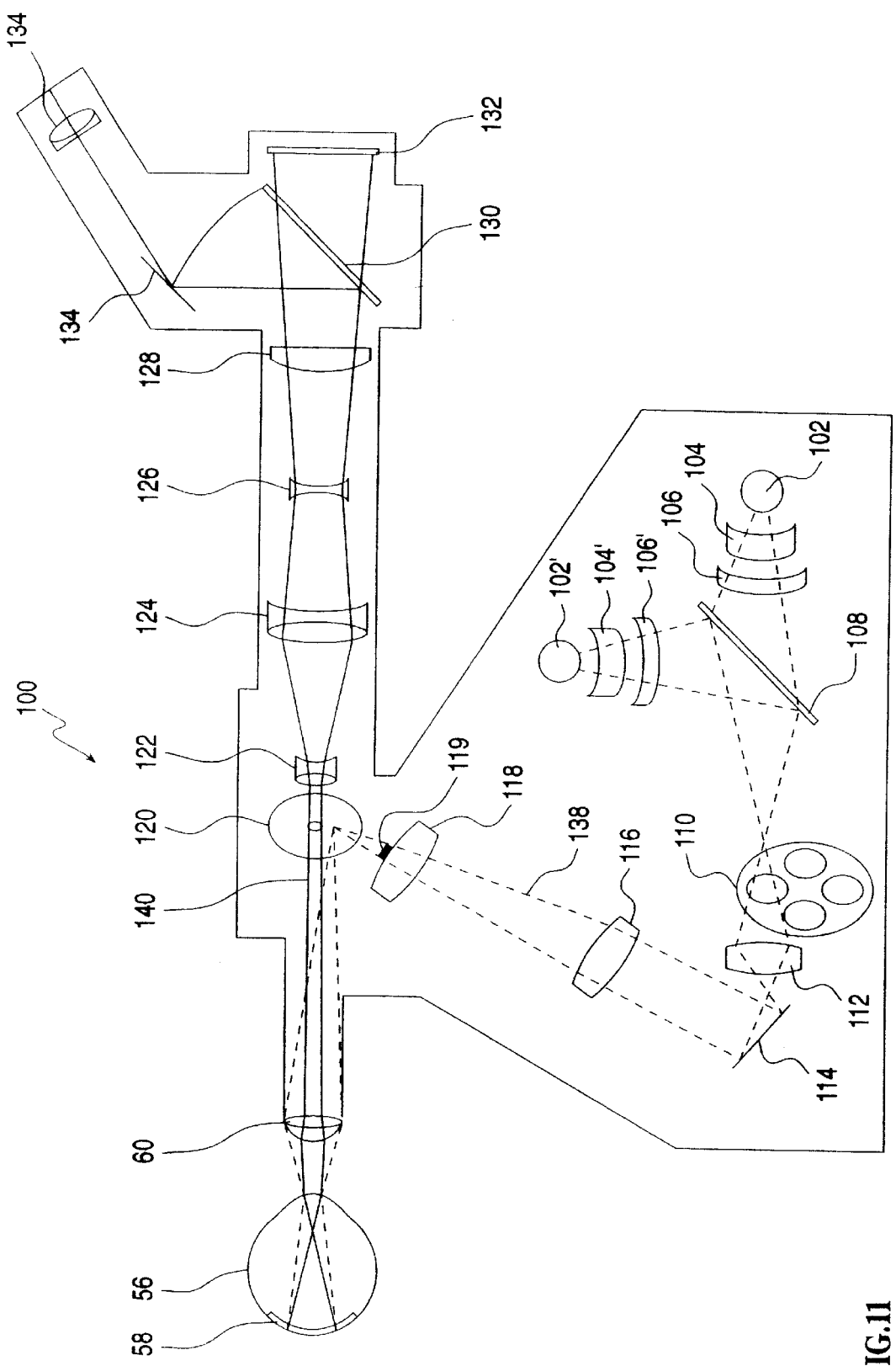
FIG. 11 shows a prior art fundus camera

FIG. 11 adapted from P. J. Saine and M. E. Tyler, *Ophthalmic Photography, Butterworth-Heinemann*, 1997, p. 15 FIG. 2—2, shows a prior art fundus camera 100. Illumination light 138 from a source 102 passes through lenses 104 and 106 to a beam splitter 108. Alternatively, light from a source 102' passes through lenses 104' and 106' to beamsplitter 108. From beamsplitter 108, illumination light 138 passes through a filter wheel 110 and a lens 112 and is reflected by a mirror 114. Illumination light 138 then passes through lenses 116 and 118. Lens 118 includes a mask 119 to turn illumination light 138 into an annular beam, which is reflected by an annular mirror 120 via an objective lens 60 into an eye 56, where illumination light impinges on ocular fundus tissue, specifically, a retina 58. Light 140 that is reflected from retina 58 passes back out of eye 56 and is directed by objective lens 60 axially through the central hole in mirror 120 and via lenses 124, 126 and 128 and a beamsplitter 130, either to an imaging medium 132 such as a photographic plate, or, via a mirror 134 to an eyepiece 136. Images of retina 58 are recorded on imaging medium 132 and are viewed by an operator through eyepiece 136.

Figure 5A:
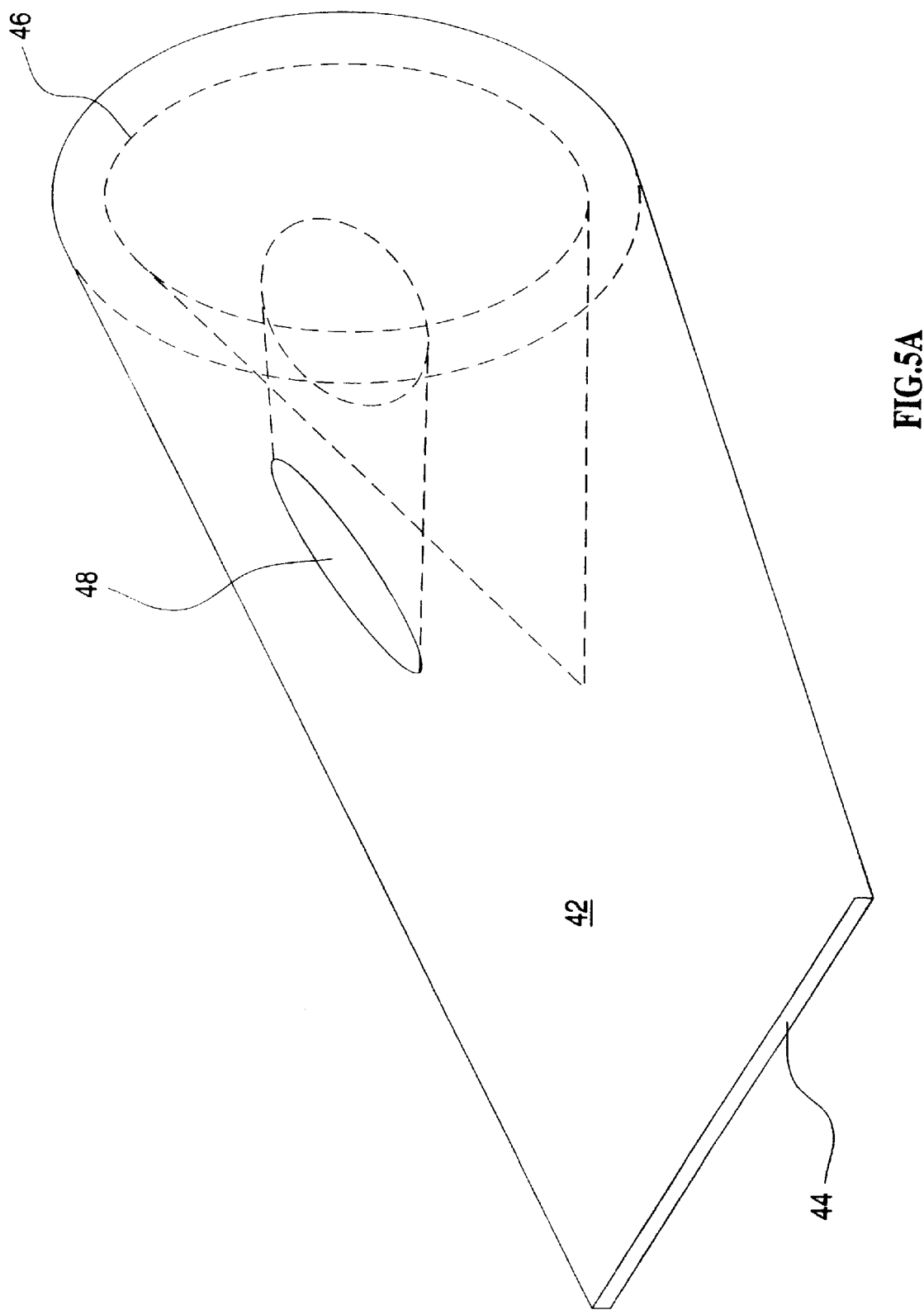
FIGS. 5A and 5B are two varieties of waveguides.
Figure 5B:
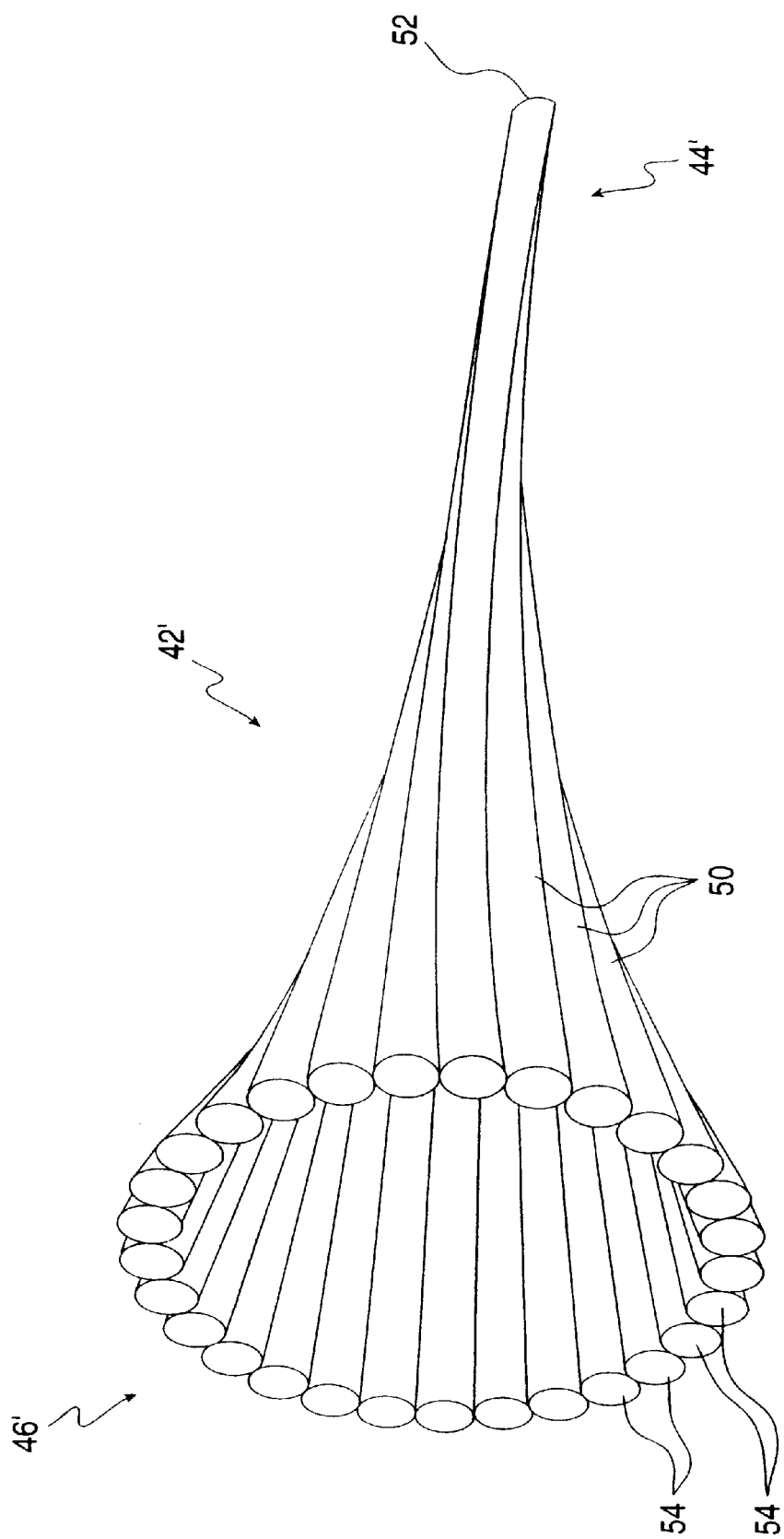

FIG. 5 shows the rest of illumination optics 14 for imaging an ocular fundus. Specifically, FIG. 5A shows an optical waveguide 42 having a linear input end 44 and an annular output end 46. Hidden surfaces and edges are drawn in FIG. 5A as phantom lines. As shown in FIG. 4, linear input end 44 is placed at line 40 so that emitted light 24 enters linear input end 44 and emerges from output end 46 as an annular beam. Waveguide 42 also is provided with an aperture 48. Light reflected from the ocular fundus through the pupil passes through the center of output end 46 and through aperture 48 to collection optics 18. Waveguide 42 is shown in FIG. 5A as a monolith. Alternatively, as shown in FIG. 5B, an optical waveguide 42' is formed as a bundle of optical fibers 50. Input ends 52 of optical fibers 50 are lined up along linear input end 44' of waveguide 42'. Output ends 54 of optical fibers 50 are disposed around the circumference of a circle at annular output end 46' of waveguide 42'.

A simple calculation illustrates the feasibility of the desired 12.5 nm spectral bandwidth of the illumination of object 16. Assume that the focal lengths f of collimating optics 14 and 18 are equal, and that the vertical widths W of the LED rows of source array 12 and input end 44 are matched. The bandpass BP of illumination optics 14 is given by $$BP = \frac{Dd \cos\Theta}{kf} \quad (11)$$

where D is the diameter of the emitting area of an LED 28, d is the spacing between the lines of diffraction grating 36, k is the diffraction order and $\Theta$ is the angle of incidence of emitted light 24 on diffraction grating 36 relative to the grating normal. The following typical parameters:

D=2.8 mm d=$\frac{1}{1200}$ mm k=1 (first order diffraction)

f=200 mm $\Theta$=45° give BP=12.4 nm as desired.

Figure 6:
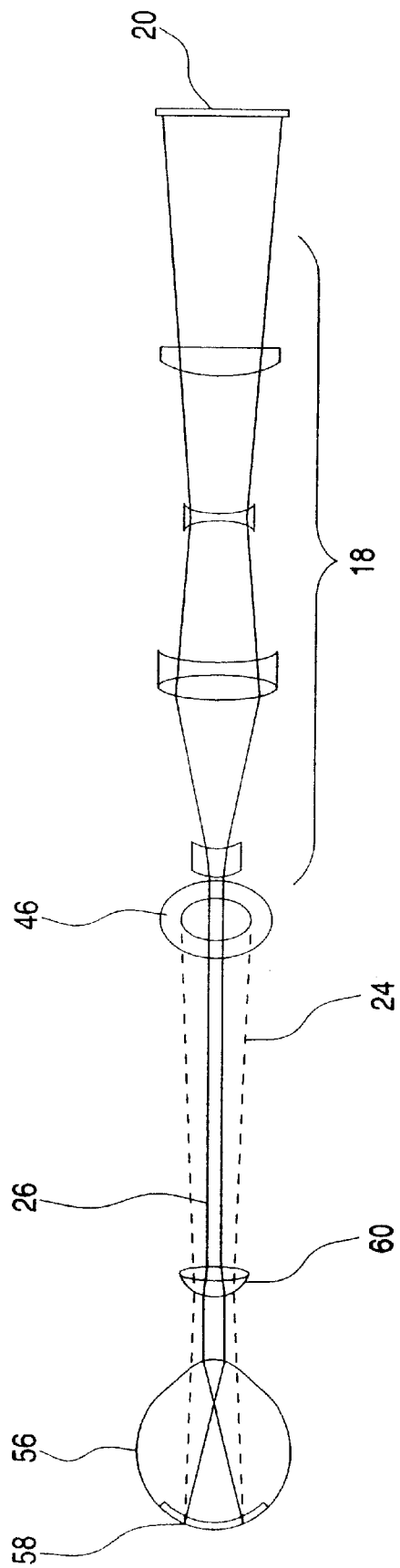
FIG. 6 illustrates part of the optics for spectral imaging of ocular fundus tissue.

FIG. 6 illustrates the use of the present invention to acquire spectral images of ocular fundus tissue, specifically, retina 58, of eye 56, using components adapted from fundus camera 100. Annular output end 46 of waveguide 42 or 42' is substituted for mirror 120. Emitted light 24 from annular output end 46 of waveguide 42 or 42' is directed by objective lens 60 through the cornea and the dilated pupil of eye 56. Reflected light 26 from retina 58 emerges from eye 56 and is directed by objective lens 60, via the central hole in output end 46 and via aperture 48, to collection optics 18 and detector array 20. Note that collection optics 18 includes lenses 122, 124, 126 and 128. Because each image of retina 58 is acquired in the desired spectral band, there is no need to correct the acquired spectra when different images are registered to compensate for motion of eye 56.

Fundus photography requires a minimum illumination intensity of about 800 $\mu$W/cm$^2$ (F. C. Delori et al., "Light levels in fundus photography and fluorescein angiography", *Vision Research* vol. 20 pp. 1099–1104 (1980). The output power density P from output end 46 or 46' in a particular spectral band is given by $$P = N \cdot SR \cdot GE \cdot TE \cdot L/A \quad (12)$$

where N is the number of LEDs 28 in one row of source array 12, SR is the selection ratio (ratio of power in the selected spectral band to total emitted power) of diffraction grating 36 or 38, GE is the grating efficiency, TE is the throughput efficiency of waveguide 44 or 44', L is the output radiated power of one LED 28 and A is the area of output end 46 or 46' from which emitted light 24 emerges. Some of these parameters are approximately the same for all the spectral bands produced by illumination optics 14. In source array 12, N=8. Typical values of GE for k=1 are at least 0.5 over the spectral range of 400 nm to 700 nm. A realistic value of TE is 0.7. A representative size of output end 46' is an outer diameter of 7 mm and an inner diameter of 3 mm, for an area A of 0.314 cm$^2$.

Figure 7:
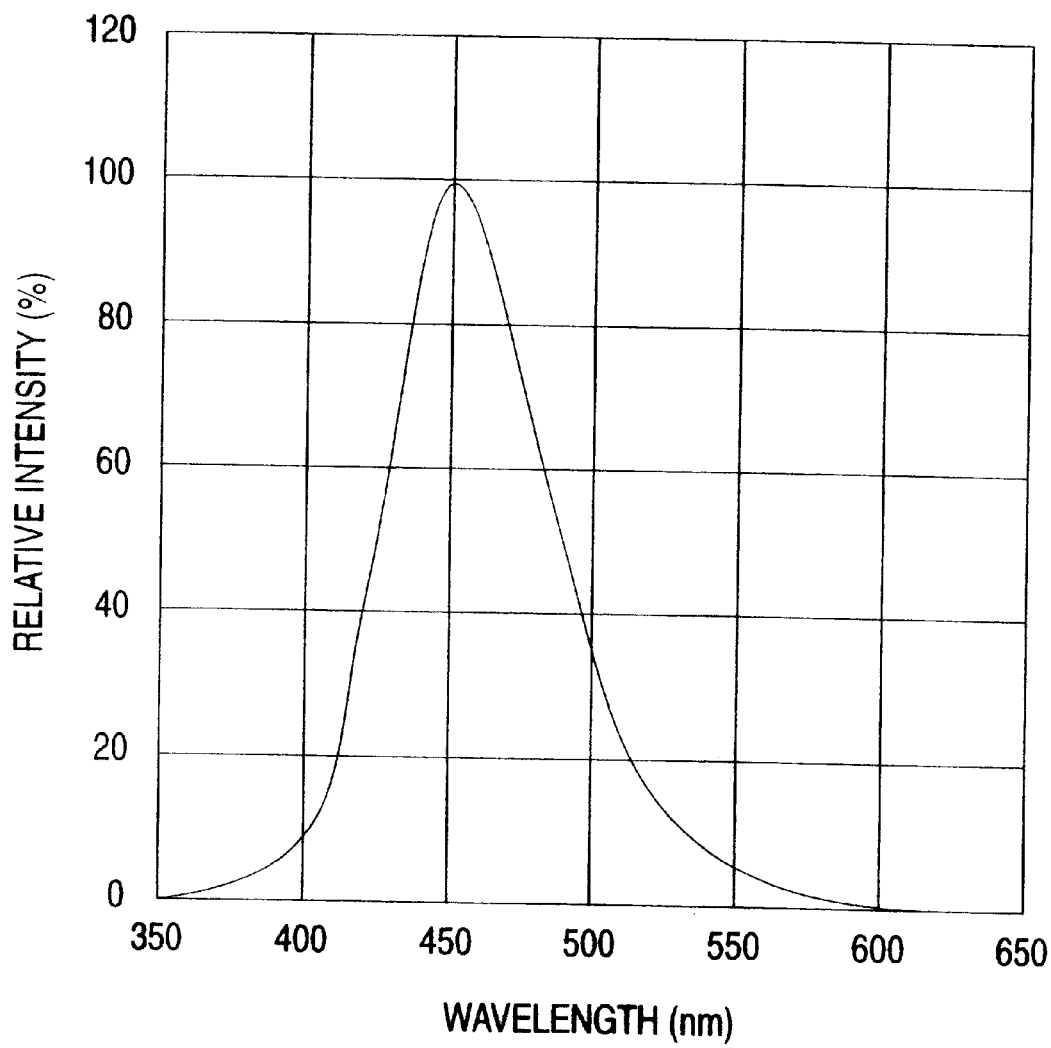
FIG. 7 shows the output spectrum of the blue LED of FIG. 2.

Because high-power LEDs are more readily available at the red end of the spectrum than at the blue end of the spectrum, it suffices to investigate the output power of a blue LED. FIG. 7 shows the spectrum of the blue LED of FIG.

2 in more detail. This LED is advertised as having an output of 1 candela. Typically, the light from an LED fills a cone with an apex angle of 50°, which is equivalent to a solid angle of 2.24 steradians, so that the power output of this LED is 3280 $\mu$W. Approximate selection ratios in the spectral bands of interest are:

| spectral band (nm) | selection ratio |
|---|---|
| 400–412.5 | .028 |
| 412.5–425 | .066 |
| 425–437.5 | .122 |
| 437.5–450 | .162 |
| 450–462.5 | .160 |
| 462.5–475 | .136 |
| 475–487.5 | .107 |
| 487.5–500 | .078 |
| 500–512.5 | .050 |
| 512.5–525 | .029 |

To obtain the desired minimum illumination intensity of 800 $\mu$W/cm$^2$, using 8 3280 $\mu$W LEDs, the minimum selection ratio is $$\frac{800 - 0.314}{8 \cdot 0.5 \cdot 0.7 \cdot 3280} = .027$$

Therefore, the present invention provides adequate illumination intensity for fundus photography, even under the least favorable circumstances of single band illumination at the shortest wavelength. LEDs 28 of the first and last rows of set 30*a* are illuminated continuously to obtain this illumination intensity in the 400–412.5 nm and 512.5–525 nm bands. The other LEDs 28 have partial illumination duty cycles. For example, to obtain the desired 800 $\mu$W/cm$^2$ in the 437.5–450 nm band, LEDs 28 of the fourth row are illuminated only a fraction of the time obtained by dividing the minimum selection ratio by the selection ratio of the fourth row: 0.027/0.162=0.17.

Alternatively, albeit less preferably, the present invention is used to acquire spectral images of ocular fundal tissue by replacing waveguide 44 or 44' with a similar waveguide with a solid output end instead of an annular output end, and substituting source array 12 and illumination optics 14 for the light source of a conventional fundus camera.

Figure 8A:
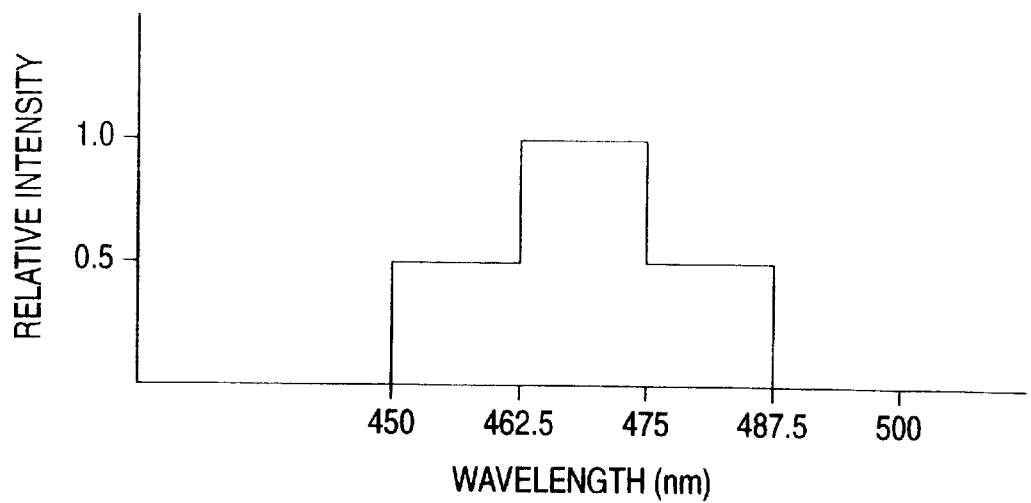
FIG. 8A is an illustrative spectral distribution of illuminating light.
Figure 8B:
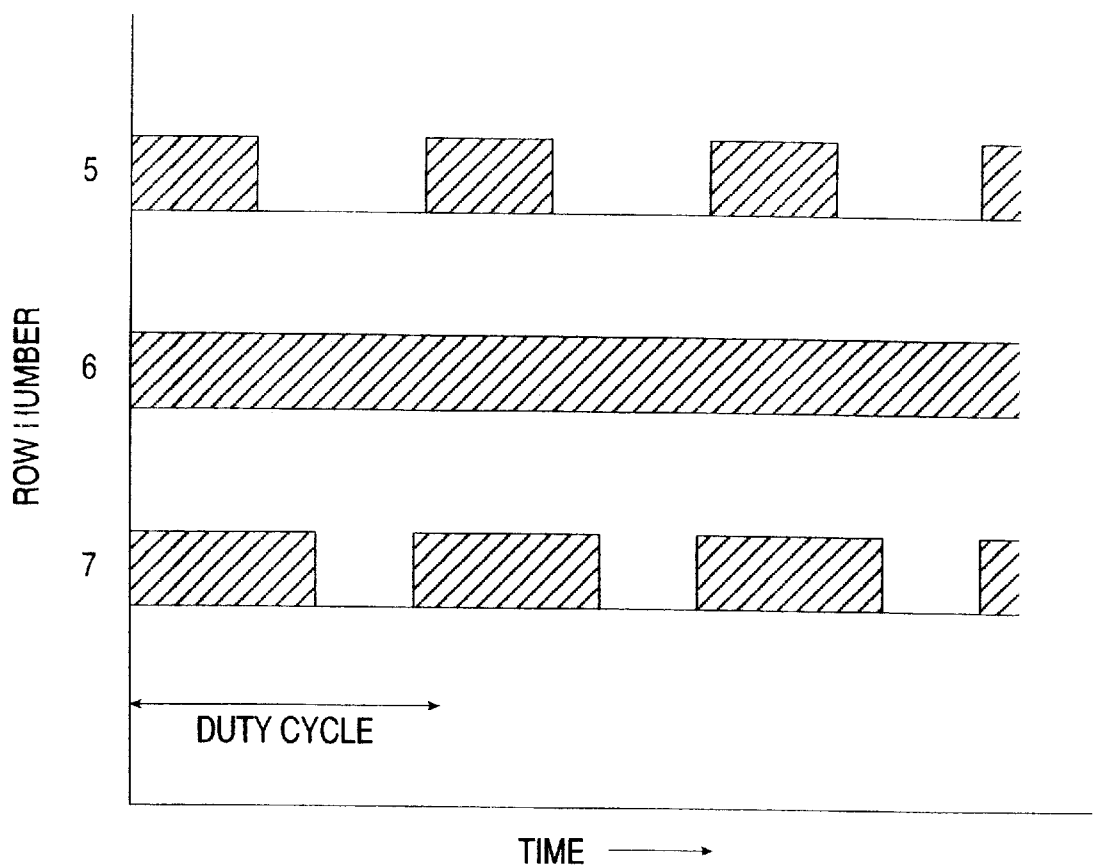
FIG. 8B shows the duty cycles of the LEDs of the fifth, sixth and seventh rows of the source array of FIG. 3 that emulates the spectral distribution of FIG. 8A.

Suppose that it is determined that the spectral distribution of FIG. 8A is particularly useful for illuminating a particular object. The present invention supplies emitted light 24 of this spectral distribution by operating LEDs 28 of the fifth, sixth and seventh rows of LED group 30*a* according to the duty cycles illustrated in FIG. 8B. Specifically, LEDs 28 of the sixth row are illuminated continuously, LEDs 28 of the fifth row are turned on 42.5% of the time and turned off 57.5% of the time, and LEDs 28 of the seventh row are turned on 63.6% of the time and turned off 36.4% of the time. As long as the duration of one on-off cycle is significantly shorter than the sampling time of detector array 20, the effective spectral distribution of emitted light 24 is the time average of the actual spectral distribution of emitted light 24, i.e., the desired spectral distribution of FIG. 8A. Typically, the sampling time of detector array 20 is on the order of 20 milliseconds. If the images are viewed directly by the operator, the on-off cycles should be significantly shorter than 100 milliseconds, the approximate integration time of the human eye.

Figure 10:
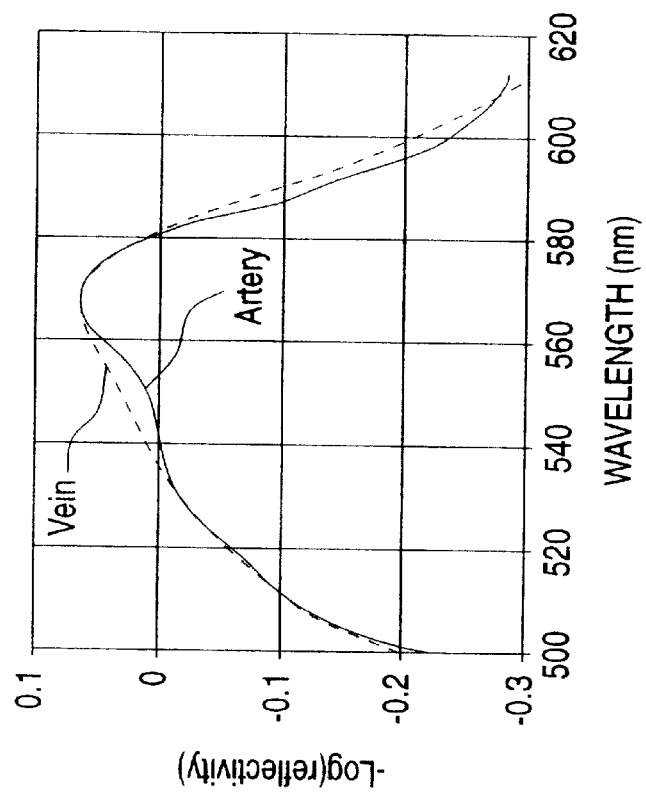
FIG. 10 shows negative log reflectances of an artery pixel and a vein pixel as functions of wavelength.
Figure 9:
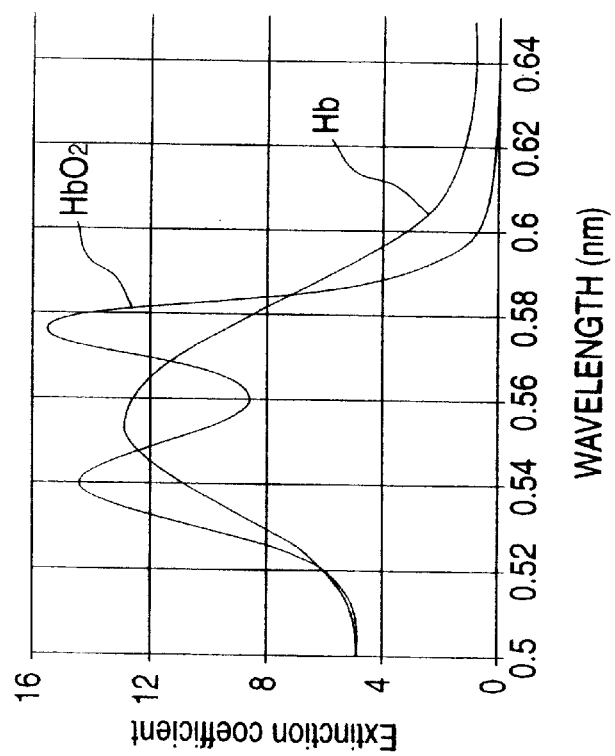
FIG. 9 shows extinction coefficients of hemoglobin (Hb) and oxyhemoglobin ($HbO_2$) as functions of wavelength.

The alternative embodiment of device 10, in which an operator views the two-dimensional images directly via collection optics 18, allows a mode of operation in which the object is illuminated successively and repeatedly with emitted light 24 of two or more different spectral distributions to enhance the contrast between different features of the object, thereby allowing the operator to distinguish features that are illuminated differentially by the several spectral distributions. For example, arteries and veins in the ocular fundus are thus distinguished visually on the basis of their different reflectivity spectra. FIG. 9 shows hemoglobin (Hb) and oxyhemoglobin (HbO$_2$) extinction coefficients, as functions of wavelength. Peaks in the extinction coefficient correspond to dips in the reflectance spectrum. Arteries, which carry oxygenated blood, and veins, which carry deoxygenated blood, therefore have different reflectivity spectra, as shown in FIG. 10, taken from co-pending U.S. patent application Ser. No. 08/942,122. FIG. 10 shows the negative log of reflectivity spectra of an artery pixel and a vein pixel as acquired by the device of U.S. Pat. No. 5,539,517. If the ocular fundus is illuminated successively and repeatedly with light 24 whose negative log spectral distribution first resembles the curve labeled "Artery" in FIG. 10 and then resembles the curve labeled "Vein" in FIG. 10, the operator sees alternating images of the ocular fundus in which, first, the arteries are enhanced relative to the veins, and then, the veins are enhanced relative to the arteries.

Figure 12:
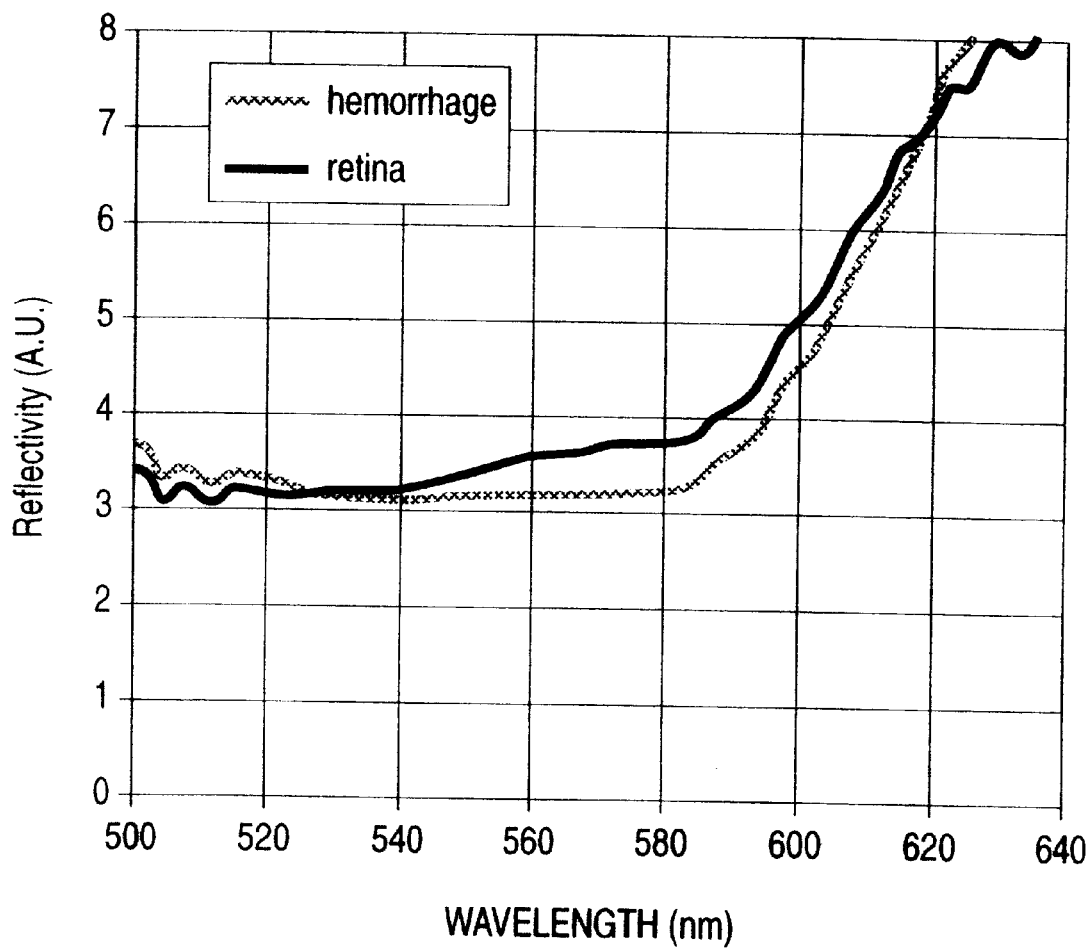
FIG. 12 shows the reflectivity spectra of a normal retina and of a retinal hemorrhage.

Similarly, if a certain pathology is associated with a unique reflectivity spectrum, tissue exhibiting that pathology is distinguished from normal tissue by alternating between illuminating the ocular fundus with light 24 whose spectral distribution resembles the reflectivity spectrum of pathological tissue and illuminating the ocular fundus with light 24 whose spectral distribution resembles the reflectivity spectrum of normal tissue. FIG. 12, which shows the reflectivity spectra of a normal retina and of a retinal hemorrhage, shows that this method provides useful additional information in the diagnosis of diabetic retinopathy.

In another application of this mode of operation, if different depths of the object have different transmissivity and reflectivity spectra, successive images correspond to successive depths in the object. This is in fact the case with the ocular fundus: the light reflected from deeper layers of the retina tends to be redder than light reflected from shallower layers of the retina (Saine and Tyler, op. cit., p. 72).

FIGS. 10 and 12 are examples of pairs of features with closely related reflectivity spectra: an artery vs. a vein in FIG. 10 and normal retinal tissue vs. hemorrhaged retinal tissue in FIG. 12. If a feature of an object must be identified from among a large number of classes of features with different but closely related reflectivity spectra, the mathematical technique of decorrelation is used to design a smaller number of synthetic reflectivity spectra that embody all the useful information contained in the larger collection of closely related reflectivity spectra. This technique is described, inter alia, in U.S. Pat. No. 5,719,024, which is incorporated by reference for all purposes as if fully set forth herein, in the context of spectral imaging of fluorescence from chromosomes labeled with whole chromosome probes. The object is illuminated successively with spectral distributions designed in accordance with each of the synthetic reflectivity spectra. The resulting images contain all of the useful information that can be used to classify the features of the object. Because the number of synthetic reflectivity spectra typically is much smaller than the number of individual spectral bands that are spanned by the original, closely related reflectivity spectra, illuminating the object with synthetic spectral distributions in this manner and classifying the features of the object on the basis of the images thus acquired is more efficient, in terms of both data acquisition and data processing, than illuminating the object sequentially with the individual spectral bands and then classifying the features of the object by comparing its measured reflectivity spectrum with the original, closely related reflectivity spectra.

While the invention has been described with respect to a limited number of embodiments, it will be appreciated that many variations, modifications and other applications of the invention may be made.

What is claimed is:

1. A device for spectral imaging of an object, comprising:
   (a) a plurality of sets of light sources for producing light in a like plurality of separate spectral bands, each of said sets including at least one of said light sources for emitting light in said spectral band of said each set;
   (b) an illumination mechanism for directing at least a portion of said emitted light at the object, thereby illuminating the object, the object producing radiated light in response to said illumination, said illumination mechanism being operative to direct said emitted light from all of said sets at a common line, said illumination mechanism including a waveguide having a linear input end coincident with said common line, said waveguide including a plurality of optical fibers; and
   (c) an imaging mechanism for detecting said radiated light and transforming said radiated light into at least one image of the object.

2. The device of claim 1, wherein said light sources include LEDs.

3. The device of claim 1, wherein said illumination mechanism includes a diffraction grating.

4. The device of claim 3, wherein said diffraction grating is operative to select a subband of at least one of said spectral bands for said illumination of the object.

5. The device of claim 1, wherein said illumination mechanism is operative to direct an annular beam of said at least portion of said emitted light at the object.

6. The device of claim 5, wherein said illumination mechanism includes a waveguide having an annular output end for forming said annular beam.

7. The device of claim 6, wherein said waveguide includes a plurality of optical fibers, each of said optical fibers having an output end, said output ends being disposed along a circle to form said annular output end of said waveguide.

8. The device of claim 1, wherein said imaging mechanism includes an array of detectors.

9. The method of claim 8, wherein said array is two-dimensional.

10. The device of claim 1, incorporated in a medical imaging apparatus.

11. The device of claim 10, wherein said medical imaging apparatus is a fundus camera.

12. The device of claim 10, wherein said medical imaging apparatus is an endoscope.

13. The device of claim 1, wherein each of said sets includes at least two of said light sources.

14. The device of claim 1, wherein each said at least one image is two-dimensional.

15. A method of imaging an object, comprising the steps of:
   (a) producing illumination light in a plurality of spectral bands, using, for each of said spectral bands, at least one light source specific to said each spectral band;
   (b) illuminating the object with at least a portion of said illumination light, the object producing radiated light in response to said illumination light; and
   (c) detecting said radiated light so as to produce at least one image of the object;
wherein the object is illuminated successively in accordance with a plurality of preselected spectral distributions, the object being illuminated simultaneously with said illumination light of said spectral bands in accordance with each said preselected spectral distribution, said successive illuminating of the object in accordance with said plurality of preselected spectral distributions being effected at least twice.

16. The method of claim 15, wherein each of said at least one light source includes an LED.

17. The method of claim 15, wherein the object is illuminated sequentially with said illumination light of each of said spectral bands.

18. The method of claim 17, wherein said detecting of said radiated light is coordinated with said sequential illumination to produce, for each said spectral band, a corresponding said at least one image of the object.

19. The method of claim 15, wherein said spectral distribution is preselected by steps including decorrelation of a plurality of reflectivity spectra.

20. The method of claim 15, wherein said illuminating of the object is effected by steps including:
   (i) forming an annular beam of said illumination light, and
   (ii) directing said annular beam at the object.

21. The method of claim 20, wherein said forming of said annular beam is effected by steps including:
   (A) providing a waveguide including an input end and an annular output end, and
   (B) introducing said illumination light to said input end of said waveguide, said illumination light then emerging from said output end of said waveguide as said annular beam.

22. The method of claim 15, wherein said producing of said illumination light is effected by operating said at least one light source of said each spectral band according to a duty cycle that results in said illuminating of the object being effected with a preselected spectral distribution.

23. The method of claim 22, wherein said spectral distribution includes a plurality of said spectral bands.

24. The method of claim 15, wherein said producing of said illumination light is effected by providing said at least one light source of said each spectral band with an electrical current level that results in said illuminating of the object being effected with a preselected spectral distribution.

25. The method of claim 24, wherein said spectral distribution includes a plurality of said spectral bands.

26. The method of claim 15, wherein said illumination is produced using at least two said light sources specific to each said spectral band.

27. The method of claim 15 wherein each said at least one image is two-dimensional.

28. The method of claim 15, wherein said spectral distribution includes a plurality of said spectral bands.

29. A method of imaging eye tissue of an eye including a pupil, comprising the steps of:
   (a) producing illumination light in a plurality of spectral bands, using, for each of said spectral bands, at least one light source specific to said each spectral band;
   (b) forming an annular beam of said illumination light;
   (c) directing said annular beam at the eye tissue via the pupil to illuminate the eye tissue sequentially with said illumination light of each of said spectral bands;
   (d) collecting light reflected from the eye tissue via the pupil; and (e) detecting said reflected light so as to produce at least one image of the eye tissue, said detecting of said reflected light being coordinated with said sequential illumination to produce, for each said spectral band, a corresponding said at least one image of the eye tissue.

30. The method of claim 29, wherein each of said at least one light source includes an LED.

31. The method of claim 29, wherein the eye tissue is illuminated simultaneously with said illumination light of said spectral bands in accordance with a preselected spectral distribution.

32. The method of claim 31, wherein the eye tissue is illuminated successively in accordance with a plurality of said preselected spectral distributions.

33. The method of claim 32, wherein said successive illuminating of the eye tissue in accordance with said plurality of said preselected spectral distributions is effected at least twice.

34. The method of claim 31, wherein said spectral distribution is preselected by steps including decorrelation of a plurality of reflectivity spectra.

35. The method of claim 31, wherein said spectral distribution includes a plurality of said spectral bands.

36. The method of claim 29, wherein said forming of said annular beam is effected by steps including:
   (i) providing a waveguide including an input end and an annular output end, and
   (ii) introducing said illumination light to said input end of said waveguide, said illumination light then emerging from said output end of said waveguide as said annular beam.

37. The method of claim 29, wherein said producing of said illumination light is effected by operating said at least one light source of said each spectral band according to a duty cycle that results in said illuminating of the object being effected with a preselected spectral distribution.

38. The method of claim 37, wherein said spectral distribution includes a plurality of said spectral bands.

39. The method of claim 29, wherein said producing of said illumination light is effected by providing said at least one light source of said each spectral band with an electrical current level that results in said illuminating of the object being effected with a preselected spectral distribution.

40. The method of claim 39, wherein said spectral distribution includes a plurality of said spectral bands.

41. The method of claim 29, wherein said illumination is produced using at least two said light sources specific to each said spectral band.

42. The method of claim 29, wherein each said at least one image is two-dimensional.

43. A method of imaging an object having at least one of a plurality of features, each of the features having a certain reflectivity spectrum, comprising the steps of:
   (a) producing illumination light in a plurality of spectral distributions, each said spectral distribution being in accordance with at least one of the reflectivity spectra;
   (b) illuminating the object with said illumination light successively at each of said plurality of spectral distributions, the object producing radiated light in response to said illumination; said successive illuminating of the object at each said spectral distribution being effected at least twice, and
   (c) detecting said radiated light so as to produce at least one image of the object.

44. The method of claim 43, wherein said producing of said illumination light is effected using a plurality of sets of at least one light source, said at least one light source of each said set all emitting in a common spectral band, each said set emitting in a different spectral band.

45. The method of claim 44, wherein each said set includes at least two said light sources.

46. The method of claim 43, wherein each of said at least one source includes an LED.

47. The method of claim 43, wherein said spectral distribution is obtained by steps including decorrelation of said reflectivity spectra.

48. The method of claim 43, wherein said spectral distribution includes a plurality of spectral bands.

49. The method of claim 43, wherein each said at least one image is two-dimensional.

50. An improved fundus camera of the type in which an annular beam of light is directed at eye tissue and light reflected from the eye tissue travels axially through the annular beam, the improvement comprising a waveguide having an annular output end wherefrom the annular beam of light emerges, said waveguide including a plurality of optical fibers.

51. The fundus camera of claim 50, wherein said waveguide has a linear input end.

52. The fundus camera of claim 50, wherein said waveguide includes an aperture wherethrough the reflected light travels.

53. The fundus camera of claim 50, wherein each of said optical fibers has an output end, said output ends being arranged along a circumference of a circle to produce the annular beam of light.

54. A method of imaging an object having a plurality of features, each feature having a reflectivity spectrum from among a larger plurality of reflectivity spectra, comprising the steps of:
   (a) producing illumination light at each of a plurality of spectral distributions, each of said spectral distributions being in accordance with at least one of said larger plurality of reflectivity spectra, said plurality of spectral distributions being obtained by steps including decorrelation of said larger plurality of reflectivity spectra;
   (b) successively illuminating the object with said illumination light at each of said plurality of spectral distributions, the object producing radiated light in response to said illumination; and
   (c) detecting said radiated light so as to produce at least one image of the object.

55. The method of claim 54, wherein said successive illuminating of the object at said each spectral distribution is effected at least twice.

56. The method of claim 54, wherein each said at least one image is two-dimensional.

57. The method of claim 54, wherein each said spectral distribution includes a plurality of spectral bands.

58. A device for spectral imaging of an object, comprising:
   (a) a plurality of sets of light sources for producing light in a like plurality of separate spectral bands, each of said sets including at least one of said light sources for emitting light in said spectral band of said each set;
   (b) an illumination mechanism for directing an annular beam of at least a portion of said emitted light at the object, thereby illuminating the object, said illumination mechanism including a waveguide that includes a plurality of optical fibers, each of said optical fibers having an output end, said output ends of said optical fibers being disposed along a circle to form an annular output end of said waveguide for forming said annular beam, the object producing radiated light in response to said illumination; and (c) an imaging mechanism for detecting said radiated light and transforming said radiated light into at least one image of the object.

59. A device for spectral imaging of an object, comprising:

(a) a plurality of sets of light sources for producing light in a like plurality of separate spectral bands, each of said sets including at least one of said light sources for emitting light in said spectral band of said each set;

(b) an illumination mechanism for directing at least a portion of said emitted light at the object, thereby illuminating the object, the object producing radiated light in response to said illumination; and (c) an imaging mechanism for detecting said radiated light and transforming said radiated light into at least one image of the object;

wherein the device is incorporated in a fundus camera.

60. A device for spectral imaging of an object, comprising:

(a) a plurality of sets of light sources for producing light in a like plurality of separate spectral bands, each of said sets including at least one of said light sources for emitting light in said spectral band of said each set;

(b) an illumination mechanism for directing at least a portion of said emitted light at the object, thereby illuminating the object, the object producing radiated light in response to said illumination; and (c) an imaging mechanism for detecting said radiated light and transforming said radiated light into at least one image of the object;

wherein the device is incorporated in an endoscope.

61. A method of imaging an object, comprising the steps of:

(a) producing illumination light in a plurality of spectral bands, using, for each of said spectral bands, at least one light source specific to said each spectral band;

(b) illuminating the object with at least a portion of said illumination light, the object producing radiated light in response to said illumination light; and (c) detecting said radiated light so as to produce at least one image of the object;

wherein the object is illuminated simultaneously with said illumination light of said spectral bands in accordance with a spectral distribution that is preselected by steps including decorrelation of a plurality of reflectivity spectra.

62. A method of imaging eye tissue of an eye including a pupil, comprising the steps of:

(a) producing illumination light in a plurality of spectral bands, using, for each of said spectral bands, at least one light source specific to said each spectral band;

(b) forming an annular beam of said illumination light;

(c) directing said annular beam at the eye tissue via the pupil to illuminate the eye tissue;

(d) collecting light reflected from the eye tissue via the pupil; and (e) detecting said reflected light so as to produce at least one image of the eye tissue;

wherein the eye tissue is illuminated successively in accordance with a plurality of preselected spectral distributions, the eye tissue being illuminated simultaneously with said illumination light of said spectral bands in accordance with each said preselected spectral distribution, said successive illuminating of the object in accordance with said plurality of preselected spectral distributions being effected at least twice.

63. A method of imaging eye tissue of an eye including a pupil, comprising the steps of:

(a) producing illumination light in a plurality of spectral bands, using, for each of said spectral bands, at least one light source specific to said each spectral band;

(b) forming an annular beam of said illumination light;

(c) directing said annular beam at the eye tissue via the pupil to illuminate the eye tissue;

(d) collecting light reflected from the eye tissue via the pupil; and (e) detecting said reflected light so as to produce at least one image of the eye tissue;

wherein the eye tissue is illuminated simultaneously with said illumination light of said spectral bands in accordance with a spectral distribution that is preselected by steps including decorrelation of a plurality of reflectivity spectra.

64. A method of imaging an object having at least one of a plurality of features, each of the features having a certain reflectivity spectrum, comprising the steps of:

(a) producing illumination light having a spectral distribution in accordance with at least one of the reflectivity spectra, said spectral distribution being obtained by steps including decorrelation of said at least one reflectivity spectrum;

(b) illuminating the object with said illumination light, the object producing radiated light in response to said illumination; and (c) detecting said radiated light so as to produce at least one image of the object.

65. A method of imaging an object having a plurality of features, each feature having a reflectivity spectrum from among a larger plurality of reflectivity spectra, comprising the steps of:

(a) producing illumination light at each of a plurality of spectral distributions, each of said spectral distributions being in accordance with at least one of said larger plurality of reflectivity spectra;

(b) successively illuminating the object with said illumination light at each of said plurality of spectral distributions, the object producing radiated light in response to said illumination, said successive illuminating of the object at each said spectral distribution being effected at least twice; and (c) detecting said radiated light so as to produce at least one image of the object.

* * * * *